US00PP10455P

United States Patent [19]

Vlielander

[11] Patent Number: Plant 10,455

[45] Date of Patent: Jun. 16, 1998

[54] KALANCHOE PLANT NAMED 'IZTAC '

[75] Inventor: Ike Vlielander, De Lier, Netherlands

[73] Assignee: Fides Beheer B.V., De Lier, Netherlands

[21] Appl. No.: 810,507

[22] Filed: Feb. 27, 1997

[51] Int. Cl.[6] ..... A01H 5/00

[52] U.S. Cl. ..... Plt./87.15

[58] Field of Search ..... Plt./87.15

*Primary Examiner*—James R. Feyrer
*Attorney, Agent, or Firm*—C. A. Whealy

[57] ABSTRACT

A distinct cultivar of Kalanchoe plant named 'Iztac', characterized by its dark hot pink flower color; vigorous plant growth habit and rapid growth rate; freely branching habit with shoots forming at every node; uniform plant habit and inflorescence display; dark green glossy leaves; proportional leaf size to plant size; suitable for various container sizes from 10 to 15 cm; floriferous with numerous flowers per plant; dark red peduncles; and excellent postproduction longevity.

1 Drawing Sheet

The present invention relates to a new and distinct cultivar of Kalanchoe plant, botanically known as *Kalanchoe blossfeldiana* Adans., and hereinafter referred to by the cultivar name 'Iztac'.

The new cultivar is a product of a planned breeding program conducted by the inventor in De Lier, The Netherlands. The objective of the breeding program was to create new Kalanchoe cultivars having a uniform plant habit, good flower and foliage colors and good postproduction longevity.

The new cultivar originated from a cross made by the inventor of the nonpatented Kalanchoe cultivar 'Aroi' as the male or pollen parent with the nonpatented Kalanchoe cultivar 'Viti' as the female or seed parent.

The cultivar 'Iztac' was discovered and selected by the inventor as a flowering plant within the progeny of the stated cross in a controlled environment in De Lier, The Netherlands. Asexual reproduction of the new cultivar by terminal cuttings taken at De Lier, The Netherlands, has shown that the unique features of this new Kalanchoe are stable and reproduced true to type in successive generations.

The cultivar 'Iztac' has not been observed under all possible environmental conditions. The phenotype may vary somewhat with variations in environment such as temperature, daylength and light intensity, without, however, any variance in genotype. The following observations, measurements and comparisons describe plants grown in De Lier, The Netherlands, under commercial practice in a glass-covered greenhouse with day temperatures ranging from 19 to 21C. and night temperatures of 18 to 19C.

The following traits have been repeatedly observed and are determined to be the unique characteristics of 'Iztac'. These characteristics in combination distinguish 'Iztac' as a new and distinct cultivar:

1. Dark hot pink flower color.
2. Vigorous plant growth habit and rapid growth rate.
3. Freely branching habit with shoots forming at every node. Plants do not require pinching.
4. Uniform plant habit and inflorescence display.
5. Dark green glossy leaves.
6. Proportional leaf size to plant size.
7. Suitable for various container sizes from 10 to 15 cm.
8. Floriferous with numerous flowers per plant.
9. Dark red peduncles.
10. Excellent postproduction longevity.

The new Kalanchoe is most similar in flower color to the commercial cultivar, 'Kiebessy' (disclosed in U.S. Plant Pat. No. 7,767). However, in side-by-side comparisons in De Lier, The Netherlands, plants of the new Kalanchoe were more freely branching, had lighter green adaxial leaf surfaces, had longer and narrower leaves, larger flowers, more intense flower color, and flowered earlier.

The accompanying colored photograph illustrates the overall appearance of the new cultivar, showing the colors as true as it is reasonably possible to obtain in colored reproductions of this type.

The photograph comprises a top perspective view of a typical potted plant of 'Iztac' taken under natural light conditions at approximately noon in De Lier, The Netherlands. Flower and foliage colors in the photograph may appear different from the actual colors due to light reflectance.

In the following description, color references are made to The Royal Horticultural Society Colour Chart except where general terms of ordinary dictionary significance are used. Measurements and numerical values represent averages for twelve typical plants in 10.5-cm containers that were grown during the months of December to April. Plants were exposed to four weeks of long day/short nights followed by eight weeks of short day/long night photoperiodic treatments and treated with daminozide growth retardant at a rate of 4 grams per liter.

Botanical classification: *Kalanchoe blossfeldiana* Adans. cultivar 'Iztac'.

Parentage:

*Male or pollen parent.*—*Kalanchoe blossfeldiana* cultivar Adans. 'Aroi' (not patented).

*Female or seed parent.*—*Kalanchoe blossfeldiana* cultivar Adans. 'Viti' (not patented).

Propagaton:

*Type cutting.*—Terminal cuttings.

*Time to initiate root.*—12 days at 21C. soil temperature.

*Rooting habit.*—Numerous, fine, fibrous, and well-branched.

Plant description:

*Form.*—Upright and uniform. Plant shape is an inverted triangle with a rounded apex. Actual plant shape will depend on whether or not plants are pinched (vegetative terminals removed).

*Branching habit.*—Freely branching, generally shoots formed at every node. Typically 6 to 9 lateral branches will develop with 15 to 25 leaves each. Lateral branch length is about 13 cm.

*Plant height at flowering.*—About 20 cm from soil level to top of plant, appropriate for 10 to 15-cm containers.

*Vigor.*—Vigorous and rapid growth rate.

*Crop time.*—Three to 4 weeks of long day/short night conditions followed by 7 to 11 weeks of short day/long night conditions are required to produce flowering plants. Depending on temperature and light levels, a total of 10 to 15 weeks is required.

*Foliage description.*—Leaves simple, opposite, generally symmetrical. Size: Length: About 15 cm. Width: About 9 cm. Shape: Elliptic. Apex: Obtuse. Base: Acute. Margin: Crenate. Texture: Leathery, glabrous, coriaceous and succulent. Petiole length: About 1 cm. Color: Young foliage upper surface: 147A, glossy. Young foliage lower surface: 138A. Mature foliage upper surface: 147A, glossy. Mature foliage lower surface: 138A. Petiole: 147B. Stem color: 147B. Venation upper side: 147A. Venation under side: 138A.

Flower description:

*Flower type and habit.*—Single flowers arranged in panicles, compound dichasial cymes on strong peduncles. Freely flowering and very floriferous with new buds continuing to develop. Uniform inflorescence display.

*Natural flowering season.*—Autumn/winter in Northern Hemisphere. Flower initiation and development can be induced under short day/long night conditions. Opening of new buds will continue for at least seven weeks. Individual flowers last about 18 days after opening. Flowers persistent.

*Inflorescences borne.*—Above foliage, arising from leaf axils. Inflorescence of each shoot is formed by dichotomous branching.

*Time to flower.*—Under warm growing temperatures, 25C., plants of the cultivar Iztac will start flowering after about 7 weeks of exposure to controlled photoperiods (short day/long night conditions). Under cooler growing temperatures, 20C., plants of the cultivar 'Iztac' will flower after about 11 weeks of exposure to controlled photoperiods. First flower open is the terminal flower at the main axis and is followed by the opening of the terminal flowers of the side branches of the inflorescence.

*Flower diameter.*—About 2.2 cm.

*Flower depth (height).*—About 1.4 cm.

*Quantity.*—More than 150 flowers per plant.

*Flower buds.*—Size: Length: About 1.3 cm. Width: About 3 mm. Shape: Oblong becoming tubular/ovoid with development. Rate of opening: Rapid. Color: Initially 147D becoming 58C just before opening.

*Petals.*—Quantity: Four. Size: Length: About 1 cm. Width: About 6 mm. Shape: Ovate. Apex: Acute. Margin: Entire. Texture: Glabrous, smooth, shiny and satiny. Aspect: Flat to partially upright. Color: When opening: 56B. Mature, upper surface: 58B. Mature, lower surface: 55B/55D. Fading to: 58C. After senescence: 58C.

*Sepals.*—Quantity: Four. Shape: Oblong, pointed. Apex: Acute. Margin: Entire. Texture: Glabrous, smooth and shiny. Aspect: Upright, rigid. Color: Upper side: 145D. Under side: 145D.

*Calyx.*—Size: About 1 cm. Shape: Funnel. Texture: Glabrous. Color: 58D/148B.

*Peduncle.*—Aspect: Fairly strong, erect, rigid, and upright. Length: 3 to 5 mm. Texture: Glabrous. Color: 138A.

*Reproductive organs.*—Stamens: Stamen number: Eight. Anther size: About 0.3 mm. Anther shape: Flat, elliptic. Anther color: Approximately 150D. Pollen color: Approximately 12A. Pistils: Pistil number: Four. Stigma shape: Flat. Stigma appearance: Crystalline. Stigma color: 8D. Style length: About 1 cm. Style color: 138D. Ovary number: Four-celled.

Disease Resistance: No known Kalanchoe diseases observed to date.

Seed Production: Seed production has not been observed.

It is claimed:

1. A new and distinct cultivar of Kalanchoe plant named 'Iztac', as illustrated and described.

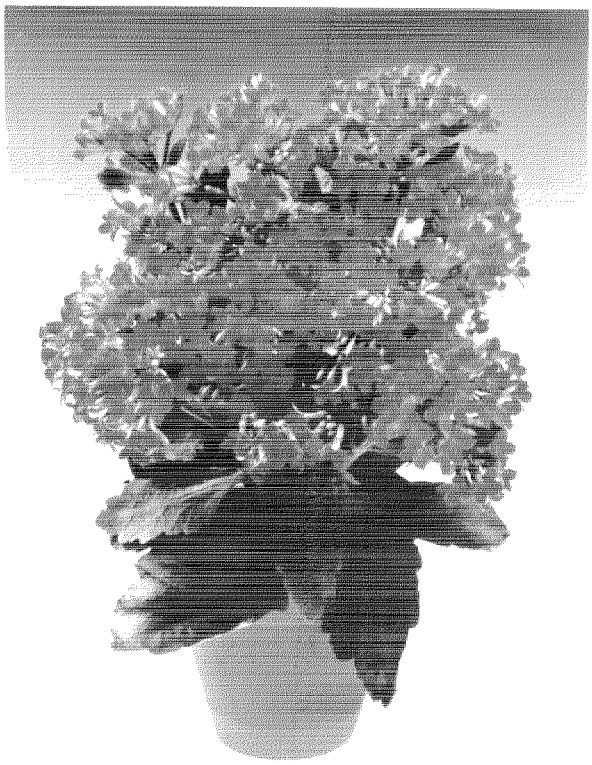

* * * * *